US012779028B2

(12) United States Patent
Bakács

(10) Patent No.: US 12,779,028 B2
(45) Date of Patent: Nov. 3, 2026

(54) USE OF A BIRNAVIRUS FOR THE TREATMENT OF A DISEASE CAUSED BY VARICELLA ZOSTER VIRUS (VZV)

(71) Applicant: HepC Terápia Kereskedelmi és Szolgáltató Zrt., Budapest (HU)

(72) Inventor: Tibor Bakács, Budapest (HU)

(73) Assignee: HepC Terápia Kereskedelmi és Szolgáltató Zrt., Budapest (HU)

(*) Notice: Subject to any disclaimer, the term of this patent is extended or adjusted under 35 U.S.C. 154(b) by 727 days.

(21) Appl. No.: 18/056,924

(22) Filed: Nov. 18, 2022

(65) Prior Publication Data

US 2023/0277650 A1 Sep. 7, 2023

Related U.S. Application Data

(60) Provisional application No. 63/281,094, filed on Nov. 19, 2021.

(51) Int. Cl.

*A61K 39/145* (2006.01)
*A61K 31/522* (2006.01)
*A61P 31/22* (2006.01)
*A61K 39/00* (2006.01)

(52) U.S. Cl.

CPC .......... *A61K 39/145* (2013.01); *A61K 31/522* (2013.01); *A61P 31/22* (2018.01); *A61K 2039/5254* (2013.01)

(58) Field of Classification Search

None
See application file for complete search history.

(56) References Cited

U.S. PATENT DOCUMENTS 8,398,969 B2 * 3/2013 Bakacs .................. C12N 15/86 435/236

OTHER PUBLICATIONS

Pikula et al. Veterinary Research, 2018, p. 1-11.*
Alexopoulou et al., Recognition of double-stranded RNA and activation of NF-kappaB by Toll-like receptor 3. Nature. Oct. 18, 2001;413(6857):732-8.
Altschul et al., Basic local alignment search tool. J Mol Biol. Oct. 5, 1990;215(3):403-10.
Altschul et al., Gapped BLAST and PSI-BLAST: a new generation of protein database search programs. Nucleic Acids Res. Sep. 1, 1997;25(17):3389-402.
Aul et al., Adverse Effects of Interferon Treatment. Springer Berlin Heidelberg, Berlin, Heidelberg; 1997:250-266.
Bakacs et al., Post-infection viral superinfection technology could treat HBV and HCV patients with unmet needs. Hepatol Med Policy. Jan. 5, 2018:3:2. 8 pages.
Brudno et al., Glocal alignment: finding rearrangements during alignment. Bioinformatics. 2003:19 Suppl 1:i54-62.
Csatary et al., Interference between human hepatitis A virus and an attenuated apathogenic avian virus. Acta Microbiol Hung. 1984;31(2):153-8.
Csatary et al., Preliminary report of a controlled trial of MTH-68/B virus vaccine treatment in acute B and C hepatitis: a phase II study. Anticancer Res. Mar.-Apr. 1998;18(2B):1279-82.
Csatary et al., Successful treatment of decompensated chronic viral hepatitis by bursal disease virus vaccine. Anticancer Res. Jan.-Feb. 199919(1B):629-33.
Dworkin et al., Recommendations for the management of herpes zoster. Clin Infect Dis. Jan. 1, 2007:44 Suppl 1:S1-26.
Eddy et al., Hmmer. Howard Hughes Medical Institute. 2023. 229 pages.
Genebank Accession No. JQ411012.1. Retrieved from the internet Mar. 11, 2024. 2 pages.
Genebank Accession No. JQ411013.1. Retrieved from the internet Mar. 11, 2024. 2 pages.
Gilden et al., Review: The neurobiology of varicella zoster virus infection. Neuropathol Appl Neurobiol. Aug. 2011;37(5):441-63.
Gluckman et al., History of the clinical use of umbilical cord blood hematopoietic cells. Cytotherapy. 2005;7(3):219-27.
Gnann et al., Clinical practice. Herpes zoster. N Engl J Med. Aug. 1, 2002;347(5):340-6.
Hornyak et al., Effective multiple oral administration of reverse genetics engineered infectious bursal disease virus in mice in the presence of neutralizing antibodies. J Gene Med. Jun.-Jul. 2015;17(6-7):116-31.
Janniger et al., Herpes Zoster Clinical Presentation. Medscape. Jul. 2021. 49 pages.
Johnson et al., Annual incidence rates of herpes zoster among an immunocompetent population in the United States. BMC Infect Dis. Nov. 6, 2015:15:502. 5 pages.
Karlin et al., Applications and statistics for multiple high-scoring segments in molecular sequences. Proc Natl Acad Sci U S A. Jun. 15, 1993;90(12):5873-7.
Kovesdi et al., Therapeutic Exploitation of Viral Interference. Infect Disord Drug Targets. 2020;20(4):423-432.
Mahalingam et al., Localization of herpes simplex virus and varicella zoster virus DNA in human ganglia. Ann Neurol. Apr. 1992;31(4):444-8.

(Continued)

*Primary Examiner* — Agnieszka Boesen

(74) *Attorney, Agent, or Firm* — Casimir Jones, S.C.; Peter J. Schlueter

(57) ABSTRACT

Provided herein are methods and compositions relating to a Birnavirus for use in the treatment of a disease caused by a Varicella zoster virus (VZV). Further, the present disclosure provides compositions and methods comprising a Birnavirus and at least one further active agent for use in the treatment of a disease caused by VSV.

8 Claims, 3 Drawing Sheets

Specification includes a Sequence Listing.

(56) References Cited

OTHER PUBLICATIONS

Maus et al., Antibody-modified T cells: CARs take the front seat for hematologic malignancies. Blood. Apr. 4, 2014;123(17):2625-35.
Nair et al., Herpes zoster on the face in the elderly. BMJ Case Rep. Oct. 19, 2014:2014:bcr2013200101. 5 pages.
Opstelten et al., Treatment of herpes zoster. Can Fam Physician. Mar. 2008;54(3):373-7.
Remington's Pharmaceutical Sciences, Mack Publishing Co. A. R Gennaro edit. 1985. TOC only 4 pages.
Rison et al., How to choose the best journal for your case report. J Med Case Rep. Jul. 22, 2017;11(1):198. 9 pages.
Thompson et al., Clustal W: improving the sensitivity of progressive multiple sequence alignment through sequence weighting, position-specific gap penalties and weight matrix choice. Nucleic Acids Res. Nov. 11, 1994;22(22):4673-80.
Vineet et al., Oro-Facial Herpes Zoster: A Case Report With a Detailed Review of Literature. Oral & Maxillofacial Pathology Journal [OMPJ]. 2013, 4(1), 346-354.

* cited by examiner

FIG. 2:
FIG. 3:
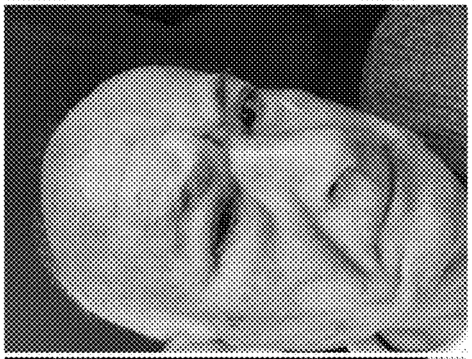
FIG. 4:
FIG. 5:
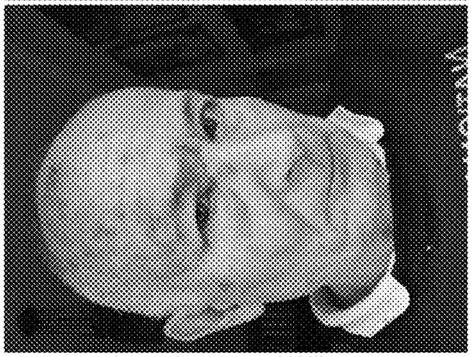
FIG. 6:
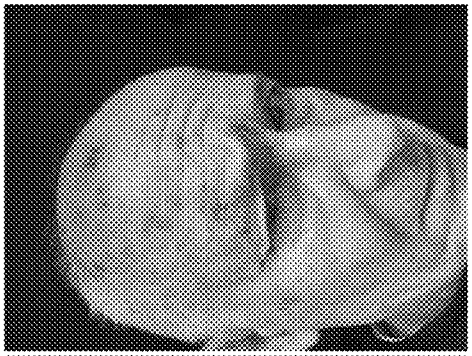
FIGS. 2-6

USE OF A BIRNAVIRUS FOR THE TREATMENT OF A DISEASE CAUSED BY VARICELLA ZOSTER VIRUS (VZV)

CROSS REFERENCE TO RELATED APPLICATIONS

This application claims priority to and the benefit of U.S. Provisional Patent Application No. 63/281,094 filed Nov. 19, 2021, which is incorporated herein by reference in its entirety for all purposes.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 9,023 Byte ASCII (XML) file named "41467_202_SequenceListing," created on Nov. 17, 2022.

FIELD

The present disclosure provides a Birnavirus for use in the treatment of a disease caused by a Varicella zoster virus (VZV). Further, the present disclosure provides compositions and methods comprising a Birnavirus and at least one further active agent for use in the treatment of a disease caused by VSV.

BACKGROUND

Herpes zoster (shingles) is a self-limiting condition caused by reactivation of the Varicella zoster virus (VZV). Shingles are characterized by grouped herpetiform vesicles developing on the erythematous base, pain in the dermatomal area of involvement, which typically affects one dermatome. The risk of VZV increases with advancing age from 0.86 per 1000 person-years in individuals <19 years of age to 12.78 per 1000 person-years among those 80 years of age and older [2]. In fact, about one-third of people are affected by shingles during their lifetime, but one-half of those who live to age 80 years. Predisposing factors for VZV reactivation are older age (shingles affects mostly people over 60 yrs.), physical trauma (including dental procedures), psychological stress, malignancy, radiation therapy and immunocompromised states (e.g., transplant recipients, steroid therapy and HIV infection).

VZV is a neurotropic herpesvirus that infects nearly all humans. Primary infection causes chickenpox (varicella). Varicella vesicles can develop on any dermatome. Cell-free VZV have therefore direct access to dorsal root, cranial nerve and autonomic nervous system ganglia along the entire neuraxis (the axial part of the central nervous system), where VZV becomes latent. Decades after primary infection, as VZV-specific host immunity declines with age, the virus may reactivate spontaneously anywhere on the body because VZV becomes latent in ganglia along the neuraxis. VZV travels from the cell bodies of the neurons to the nerve terminals in the skin characterized by dermatomal distribution of pain and rash. The course of shingles can be divided into three stages: prodromal stage, infectious rash and resolution. Early symptoms include pruritus, the involved area may be tender to palpation, mild to severe burning, throbbing or stabbing pain could occur. Prodromal illness lasts one to four days. Then, erythematous macules and papules develop and progress to infectious vesicles which last for seven to ten days. Vesicles initially are clear but eventually cloud, rupture, crust, and involute. Healing is completed in two to four weeks. While shingles is self-limiting, post-herpetic neuralgia (PHN) is a frequent complication, where pain persists for months or years after the rash has resolved.

When viral reactivation occurs in the cranial nerve (CN) V (trigeminal nerve; Gasserian ganglion) Herpes zoster ophthalmicus (HZO) develops. HZO accounts for 10-15% of zoster cases. HZO is characterized by vesicular and erythematous involvement of the CN V1 dermatome, ipsilateral forehead, and upper eyelid. Ipsilateral preauricular (occasionally submaxillary) nodal involvement is a common prodromal event, which together with pain, vesiculation, and erythema is an important symptom in establishing a diagnosis. Development of orbital edema is, however, an ophthalmologic emergency, when patients must be referred immediately for specialized evaluation and treatment. In such cases, iritis, iridocyclitis, glaucoma, and corneal tissue ulcerations may occur.

SUMMARY

Embodiments of the present disclosure include a composition comprising a strain of an Infectious Bursal Disease Virus (IBDV) for the treatment of disease caused by a Varicella zoster virus (VZV).

In some embodiments, the IBDV is an IBDV of strain 903/78 (also referred to as V903/78 or R903/78)

In some embodiments, the IBDV is derived from non-pathogenic attenuated strain 903/78 and comprises a nucleic acid sequence that is at least 80% identical to SEQ ID NO: 1 (segment A).

In some embodiments, the IBDV is derived from non-pathogenic attenuated strain 903/78 and comprises a nucleic acid sequence that is at least 80% identical to SEQ ID NO: 2 (segment B).

In some embodiments, the IBDV is derived from a recombinant Birnavirus.

In some embodiments, the IBDV is formulated for administration to a subject receiving or having received treatment for VZV.

In some embodiments, the VZV treatment is selected from the group consisting of an antiviral drug therapy, an antibacterial drug therapy, an anti-inflammatory drug therapy, antifungal drug therapy, an antipyretic agent therapy, and corticoid therapy.

In some embodiments, the VZV treatment comprises administration of acyclovir.

In some embodiments, the disease caused by the VZV is herpes zoster.

In some embodiments, the disease caused by the VZV is herpes zoster ophthalmicus.

Embodiments of the present disclosure also include a method of treating a subject having or suspected of having a disease caused by a Varicella zoster virus (VZV). In accordance with these embodiments, the method includes administering a therapeutically effective dose of composition comprising a strain of an Infectious Bursal Disease Virus (IBDV), and at least one pharmaceutically acceptable carrier or excipient.

In some embodiments of the method, the disease caused by the VZV is herpes zoster.

In some embodiments of the method, the disease caused by the VZV is herpes zoster ophthalmicus.

In some embodiments of the method, the composition is administered intravenously, subcutaneously, intradermally, intraarterially, orally, nasally, and/or by inhalation.

In some embodiments of the method, the composition is administered at a dose ranging from about $10^6$ to about $10^9$ infectious units per day.

In some embodiments of the method, the IBDV is derived from non-pathogenic attenuated strain 903/78 and comprises a nucleic acid sequence that is at least 80% identical to SEQ ID NO: 1 (segment A).

In some embodiments of the method, the IBDV is derived from non-pathogenic attenuated strain 903/78 and comprises a nucleic acid sequence that is at least 80% identical to SEQ ID NO: 2 (segment B).

In some embodiments of the method, the method further comprises administering a VZV treatment selected from the group consisting of an antiviral drug therapy, an antibacterial drug therapy, an anti-inflammatory drug therapy, antifungal drug therapy, an antipyretic agent therapy, and corticoid therapy.

In some embodiments of the method, the method further comprises administration of acyclovir.

In some embodiments of the method, the method treats at least one symptom associated with the VZV disease in the subject.

BRIEF DESCRIPTION OF THE FIGURES

FIGS. 2-6: The subject with herpes zoster ophthalmicus and periorbital edema at the peak of disease and in recovery. The pictures were made between Oct. 9, 2021, and Oct. 12, 2021.

DETAILED DESCRIPTION

Definitions

Figure 1:
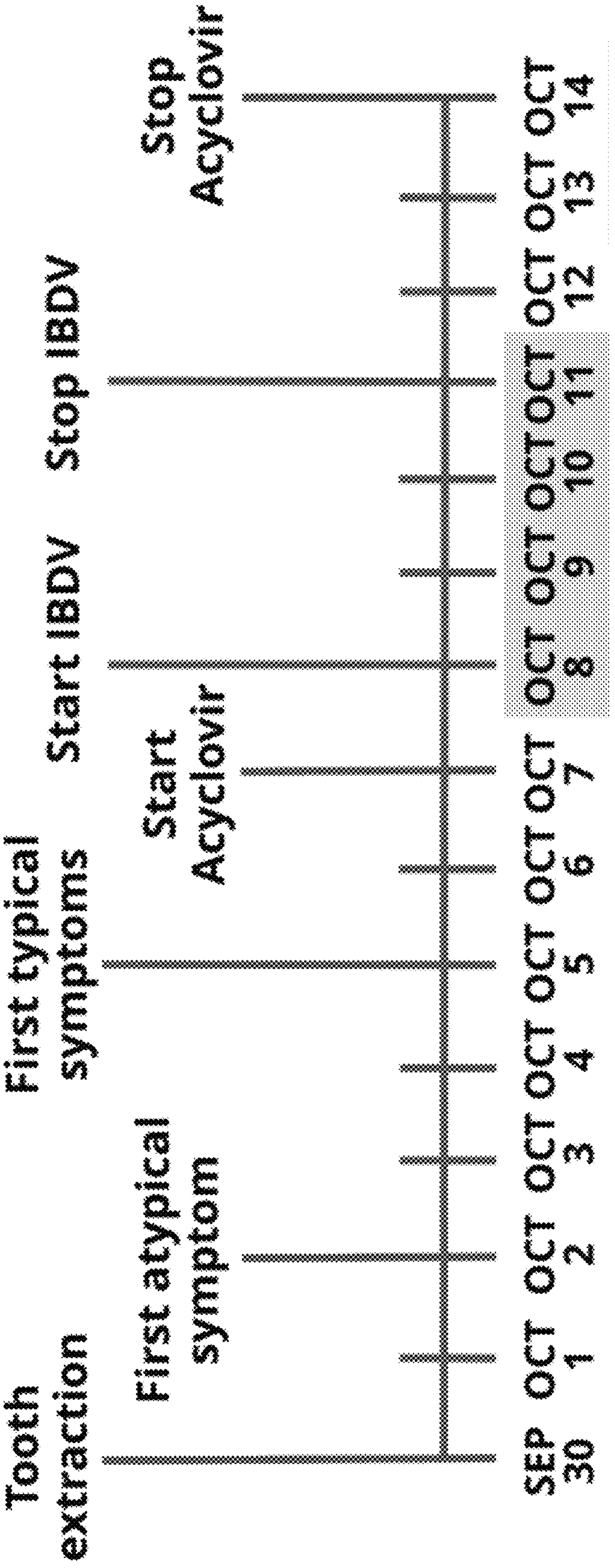
FIG. 1: Disease and treatment course. Date line of herpes zoster ophthalmicus and its treatment from September 30 to Oct. 14, 2021. Extended lines designate the start of symptoms and treatment. Days highlighted by grey designate treatment with IBDV.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Correlated to" as used herein refers to compared to.

In the context of the present disclosure, a Birnavirus can be used as a medicament, in particular for the treatment of a disease caused by a Varicella zoster virus (VZV). The term "Birnavirus," as used herein, refers to a small (about 70 nm in diameter), non-enveloped virus. It is a segmented, linear, double-stranded (ds) RNA virus. The genome is about 5.9 to 6.9 kbp in length and codes for 5 to 6 proteins in segments A (Genebank Accession Number: JQ411012.1) and B (Genebank Accession Number: JQ411013.1). Birds, fishes, and insects are described as natural hosts. The Birnavirus replication is cytoplasmic. Entry into the host cell is achieved by cell receptor endocytosis. Replication follows the double-stranded RNA virus replication model in the cytoplasm. Double-stranded RNA virus transcription is the method of transcription in cytoplasm. A Birnavirus typically releases its progeny via continuous budding of viral particles from an intact cell membrane.

In one embodiment, the Birnavirus is selected from the group consisting of an avibirnavirus, an aquabirnavirus, a Birnavirus, a dronavirus, an entomobirnavirus, a ronavirus, and a telnavirus. In one embodiment, the avibirnavirus is an Infectious Bursal Disease Virus (IBDV). In one embodiment, the IBDV is an IBDV of strain 903/78 (also referred to as V903/78 or R903/78). In one embodiment, the (genome of) IBDV of strain 903/78 comprises a nucleotide sequence comprising segment A (SEQ ID NO: 1, or a fragment thereof or a sequence having at least 80% sequence identity thereto), and/or a nucleotide sequence comprising segment B (SEQ ID NO: 2, or a fragment thereof or a sequence having at least 80% sequence identity thereto). These sequences are described in U.S. Pat. No. 8,398,969, which is herein incorporated by reference in its entirety and for all purposes.

SEQ ID NO: 1 is the following nucleic acid sequence:

```
ggatacgatcggtctgaccccgggggagtcacccggggacaggccgtcaa
ggctttgttccaggatggaactcctccttctacaacgctatcattgatgg
tcagtagagatcagacaaacgatcgcagcgatgacaaacctgcaagatca
aacccaacagattgttccgttcatacggagccttctgatgccaacaaccg
gaccggcgtccattccggacgacaccctggagaagcacactctcaggtca
gagacctcgacctacaatttgactgtgggggacacagggtcagggctaat
```

-continued tgtctttttccctggattccctggctcaattgtgggtgctcactacacac tgcagagcaatgggaactacaagttcgatcagatgctcctgactgcccag aacctaccggccagttacaactactgcaggctagtgagtcggagtctcac agtgaggtcaagcacacttcctggtggcgtttatgcactaaacggcacca taaacgccgtgaccttccaaggaagcctgagtgaactgacagatgttagc tacaatgggttgatgtctgcaacagccaacatcaacgacaaaattgggaa cgtcctagtaggggaaggggtcaccgtcctcagcttacccacatcatatg atcttgggtatgtgaggcttggtgaccccattcccgcaatagggcttgac ccaaaaatggtagccacatgtgacagcagtgacaggcccagagtctacac cataactgcagccgatgattaccaattctcatcacagtaccaaccaggtg gggtaacaatcacactgttctcagccaacattgatgccatcacaagcctc agcgttgggggagagctcgtgtttcaaacaagcgtccacggcattgtact gggcgccaccatctacctcataggctttgatgggacagcggtaatcacca gggctgtggccgcaaacaatgggctgacgaccggcaccgacaaccttatg ccattcaatcttgtgattccaacaaacgagataacccagccaatcacatc catcaaactggagatagtgacctccaaaagtggtggtcaggcaggggatc agatgtcatggtcggcaagagggagcctagcagtgacgatccatggtggc aactatccaggggccctccgtcccgtcacgctagtggcctacgaaagagt ggcaacaggatccgtcgttacggtcgctggggtgagcaacttcgagctga tcccaaatcctgaactagcaaagaacctggttacagaatacggccgattt gacccaggagccatgaactacacaaaattgatactgagtgagagggaccg tcttggcatcaagaccgtctggccaacaagggagtacactgactttcgtg aatacttcatggaggtggccgacctcaactctcccctgaagattgcagga gccttcggcttcaaagacataatccgggccataaggaggatagctgtgcc ggtggtctccacattgttcccacctgccgctcccctagcccatgcaattg gggaaggtgtagactacctgctgggcgatgaggcacaggctgcttcagga actgctcgagccgcgtcaggaaaagcaagagctgcctcaggccgcataag gcagctgactctcgccgccgacaaggggtacgaggtagtcgcgaatctat tccaggtgccccagaatcccgtagtcgacgggattcttgcttcacctggg gtactccgcggtgcacacaacctcgactgcgtgttaagagagggtgccac gctattccctgtggttattacgacagtggaagacgccatgacacccaaag cattgaacagcaaaatgtttgctgtcattgaaggcgtgcgagaagacctc caacctccatctcaaagaggatccttcatacgaactctctctggacacag agtctatggatatgctccagatggggtacttccactggagactgggagag actacaccgttgtcccaatagatgatgtctgggacgacagcattatgctg tccaaagatcccatacctcctattgtgggaaacagtggaaatctagccat agcttacatggatgtgtttcgacccaaagtcccaatccatgtggctatga cgggagccctcaatgcttgtggcgagattgagaaagtaagctttagaagc accaagctcgccactgcacaccgacttggccttaagttggctggtcccgg agcattcgatgtaaacaccgggcccaactgggcaacgttcatcaaacgtt tccctcacaatccacgcgactgggacaggctcccctacctcaacctacca -continued taccttccacccaatgcaggacgccagtaccaccttgccatggctgcatc agagttcaaagagacccccgaactcgagagtgccgtcagagcaatggaag cagcagccaacgtggacccactattccaatctgcactcagtgtgttcatg tggctggaagagaatgggattgtgactgacatggccaacttcgcactcag cgacccgaacgcccatcggatgcgaaattttcttgcaaacgcaccacaag caggcagcaagtcgcaaagggccaagtacgggacagcaggctacggagtg gaggctcggggccccacaccagaggaagcacagagggaaaaagacacacg gatctcaaagaagatggagaccatgggcatctactttgcaacaccagaat gggtagcactcaatgggcaccgagggccaagccccggccagctaaagtac tggcagaacacacgagaaataccggacccaaacgaggactatctagacta cgtgcatgcagagaagagccggttggcatcagaagaacaaatcctaaggg cagctacgtcgatctacggggctccaggacaggcagagccaccccaagct ttcatagacgaagttgccaaagtctatgaaatcaaccatggacgtggccc aaaccaagaacagatgaaagatctgctcttgactgcgatggagatgaagc atcgcaatcccaggcgggctctaccaaagcccaagccaaaacccaatgct ccaacacagagacccccctggtcggctgggccgctggatcaggaccgtctc tgatgaggaccttgagtgaggctcctgggagtctcccgacaccacccgcg caggtgtggacaccaattcggccttacaacccaaattggatccgttcgcg ggtcccct.

SEQ ID NO: 2 is the following nucleic acid sequence:

ggatacgatgggtttgaccctcagggagtcacgaattaacatggctacta ggggcgatacccgccgctggctgccacgttagtggctcctcttcttgatg attctgccaccatgagtgacattttcaacagtccacaggcgcgaagcacg atctcagcagcgttcggcataaagcctactgctggacaagacgtggaaga actcttgatccctaaagtttgggtgccacctgaggatccgcttgccagcc ctagtcgactggcaaagttcctcagagagaacggctacaaagttttgcag ccacggtctctgcccgagaatgaggagtatgagaccgaccaaatactccc agacttagcatggatgcgacagatagaaggggctgttttaaaacccactc tatctctccctattggagatcaggagtacttcccaaagtactacccaaca catcgccctagcaaggagaagcccaatgcgtacccgccagacatcgcact actcaagcagatgatttacctgtttctccaggttccagaggccaacgagg gcctaaaggatgaagtaaccctcttgacccaaaacataagggacaaggcc tatggaagtgggacctacatgggacaagcaactcgacttgtggccatgaa ggaggtcgccactggaagaaacccaaacaaggatcctctaaagcttgggt acacttttgagagcatcgcgcagctacttgacatcacactaccggtaggc ccacccggtgaggatgacaagccctgggtgccactcacaagagtgccgtc acggatgttggtgctgacgggagacgtagatggcgactttgaggttgaag attaccttcccaaaatcaacctcaagtcatcaagtggactaccatatgta ggtcgcaccaaaggagagacaattggcgagatgatagctatctcaaacca -continued

```
gtttctcagagagctatcaacactgttgaagcaaggtgcagggacaaagg
ggtcaaacaagaagaagctactcagcatgttaagtgactattggtactta
tcatgcgggcttttgtttccaaaggctgaaaggtacgacaaaagcacatg
gctcaccaagacccggaacatatggtcagctccatccccaacacacctca
tgatctctatgatcacctggcccgtgatgtccaacagcccaaataacgtg
ttgaacattgaagggtgtccatcactctacaaattcaacccgttcagagg
agggttgaacaggatcgtcgagtggatattggccccggaagaacccaagg
ctcttgtatatgcggacaacatatacattgtccactcaaacacgtggtac
tcaattgacctagagaagggtgaggcaaactgcactcgccaacacatgca
agccgcaatgtactacatactcaccagagggtggtcagacaacggcgacc
caatgttcaatcaaacatgggccacctttgccatgaacattgcccctgct
ctagtggtggactcatcgtgcctgataatgaacctgcaaattaagaccta
tggtcaaggcagcgggaatgcagccacgttcatcaacaaccacctcttga
gcacgctagtgcttgaccagtggaacctgatgagacagcccagaccagac
agcgaggagttcaaatcaattgaggacaagctaggtatcaactttaagat
tgagaggtccattgatgatatcaggggcaagctgagacagcttgtcctcc
ttgcacaaccagggtacctgagtgggggggttgaaccagaacaatccagc
ccaactgttgagcttgacctactagggtggtcagctacatacagcaaaga
tctcgggatctatgtgccggtgcttgacaaggaacgcctattttgttctg
ctgcgtatcccaagggagtagagaacaagagtctcaaatccaaagtcggg
atcgagcaggcatacaaggtagtcaggtatgaggcgttgaggttggtagg
tggttggaactacccactcctgaacaaagcctgcaagaataacgcaggcg
ccgctcggcggcatctggaggccaaggggttcccactcgacgagttccta
gccgagtggtctgagctgtcagagttcggtgaggccttcgaaggcttcaa
tatcaagctgaccgtaacatctgagagcctagccgaactgaacaagccag
tacccccaagcccccaaatgtcaacagaccagtcaacactgggggactc
aaggcagtcagcaacgccctcaagaccggtcggtacaggaacgaagccgg
actgagtggtctcgtccttctagccacagcaagaagccgtctgcaagatg
cagttaaggccaaggcagaagccgagaaactccacaagtccaagccagac
gaccccgatgcagactggttcgaaagatcagaaactctgtcagaccttct
ggagaaagccgacatcgccagcaaggtcgcccactcagcactcgtggaaa
caagcgacgctcttgaagcagttcagtcgacttccgtgtacacccccaag
tacccagaagtcaagaacccacagaccgcctccaaccccgttgttgggct
ccacctgcccgccaagagagccaccggtgtccaggccgctcttctcggag
caggaacgagcagaccaatggggatggaggccccaacacggtccaagaac
gccgtgaaaatggccaaacggcggcaacgccaaaaggagagccgctaaca
gccatgatgggaaccactcaagaagaggacactaatcccagaccccgtat
ccccggccttcgcctgcgggggccccc.
```

The similarity of nucleotide sequences, i.e., the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90:5873-5877), with hmmalign (HMMER package, http://hmmer.wustl.edu/) or with the CLUSTAL algorithm (Thompson J. D. et al. Nucleic Acids Res. 1994, 22:4673-80) available e.g. on http://www.ebi-.ac.uk/Tools/clustalw/ or on http://www.ebi.ac.uk/Tools/clustalw2/ index.html or on http://npsa-pbil.ibcp.fr/cgi-bin/npsa_automat.pl?page=/NPSA/npsa_clustalw.html. Preferred parameters used are the default parameters as they are set on http://www.ebi.ac.uk/Tools/clustalw/ or http://www.ebi.ac.uk/Tools/clustalw2/ index.html. The grade of sequence identity (sequence matching) may be calculated using e.g., BLAST, BLAT or BlastZ (or BlastX). A similar algorithm is incorporated into the BLASTN and BLASTP programs of Altschul et al. J. Mol. Biol. 1990, 215:403-410. To obtain gapped alignments for comparative purposes, Gapped BLAST is utilized as described in Altschul et al. Nucleic Acids Res. 1997, 25:3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields.

The Birnavirus of the present disclosure is apathogenic (i.e., not capable of causing disease) in humans and in the respective natural host.

As described further herein, a Birnavirus is used for the treatment of a disease caused by a Varicella zoster virus (VZV). The term "Varicella zoster virus", as used herein, refers to an alpha herpes virus that causes chickenpox and herpes zoster (shingles). Varicella is characterized by a maculopapular, vesicular rash that can be pruritic and evolves into dried crusts (scabs) over a 3- to 7-day period. Reactivation of the dormant virus results in the characteristic painful dermatomal rash of herpes zoster, which is often followed by pain in the distribution of the rash (postherpetic neuralgia).

The term "live virus" as used herein, refers to a virus that is capable of multiplying and producing progeny virus upon infection of a permissive isolated cell or a permissive cell as part of an organism. Such cell may be permissive by nature or acquire permissiveness via introduction of functional sequences required for replication or mutation/deletion of sequences that would otherwise prevent multiplication.

The term "attenuated virus", as used herein, refers to a virus with compromised virulence in the intended recipient, e.g., subject as defined herein. The Birnavirus described herein is preferably an attenuated virus and more preferably a live and an attenuated virus. In particular, the Birnavirus described herein is a replication competent live and attenuated virus.

The term "treatment", in particular "therapeutic treatment", as used herein, refers to any therapy which improves the health status and/or prolongs (increases) the lifespan of a subject suffering from a disease caused by a Varicella zoster virus. Said therapy may eliminate the disease in a subject, arrest or slow the development of the disease in a subject, inhibit the development of the disease in a subject, decrease the severity of symptoms in a subject suffering the disease, and/or decrease the recurrence in a subject who currently has or who previously has had a disease.

The present invention relates to the use of a Birnavirus as medicament. The term "medicament", as used herein, refers to a substance/combination/composition used in therapy, i.e., in treating, ameliorating or preventing a disease or disorder. In particular, the present invention relates to the use of a Birnavirus in the treatment of a disease caused by a Varicella zoster virus.

The term "monotherapy", as used herein, refers to any therapy with only one active substance. In the context of the present invention, the active substance used in monotherapy to treat a disease caused by a Varicella zoster virus is a Birnavirus. The term "combination therapy", as used herein, refers to any therapy with two or more active substances. In the context of the present invention, the active substances used in combination therapy to treat a disease caused by a Varicella zoster virus are at least one Birnavirus and at least one further active agent. The advantage of monotherapy is the possibility of a more targeted treatment of a disease, whereas combination therapy is intended to have a broader effect and also to eliminate side effects.

The term "active agent" as used herein, refers to any agent allowing the treatment, amelioration, and/or prevention of a disease caused by a Varicella zoster virus. In addition, the term "active agent", as used herein, refers to any therapeutic and/or preventive activity an agent may exhibit. The active agent is selected from the group consisting of an antiviral drug, an antibacterial drug, an anti-inflammatory drug, an antifungal drug, an antipyretic agent, and a corticoid.

The Birnavirus may be administered to a subject receiving or having received at least one further therapy against a disease caused by a Varicella zoster virus. The term "at least one further therapy against a disease caused by a Varicella zoster virus", as used herein, refers to any other therapy than the administration of a Birnavirus in order to treat a disease caused by a Varicella zoster virus. The at least one further therapy against a disease caused by a Varicella zoster virus may be selected from the group consisting of an antiviral drug therapy, an antibacterial drug therapy, an anti-inflammatory drug therapy, an antifungal drug therapy, an antipyretic agent therapy, and a corticoid therapy.

As used herein, the expressions "is for administration" and "is to be administered" have the same meaning as "is prepared to be administered". In other words, the statement that an active compound "is for administration" has to be understood in that said active compound has been formulated and made up into doses so that said active compound is in a state capable of exerting its therapeutic activity. In the context of the present invention, a Birnavirus, a combination comprising at least one Birnavirus and at least one further active agent, or a pharmaceutical composition comprising the Birnavirus or the combination is prepared to be administered.

The Birnavirus, the combination comprising at least one Birnavirus and at least one further active agent, or the pharmaceutical composition comprising the Birnavirus or the combination is in a form suitable for oral administration, nasal administration, administration by inhalation, intravascular administration, intravenous administration, intramuscular administration, intrathecal administration, subcutaneous administration, or intraperitoneal administration. The Birnavirus, the combination comprising at least one Birnavirus and at least one further active agent, or the pharmaceutical composition comprising the Birnavirus or the combination is in a form suitable for oral administration, nasal administration, or administration by inhalation.

The terms "therapeutically effective amount" or "therapeutic amount" are intended to mean that amount of a drug or pharmaceutical agent that will elicit the biological or medical response of a tissue, a system, animal or human that is being sought by a researcher, veterinarian, medical doctor or other clinician. The dosage regimen utilizing the Birnavirus or the Birnavirus in combination with the further active agent as described herein can be selected by the skilled practitioner in accordance with a variety of factors including type, species, age, weight, body mass index, sex and medical condition of the subject; the severity of the condition to be treated; the potency of the compound chosen to be administered; the route of administration; the purpose of the administration; and the renal and hepatic function of the subject. In the context of the present invention, the Birnavirus, the combination comprising at least one Birnavirus and at least one further active agent, or the pharmaceutical composition comprising the Birnavirus or the combination is administered or prepared to be administered in a therapeutically effective/therapeutic amount.

Specifically, the dose at which the Birnavirus is to be administered amounts to at least $10^6$ infectious units per day. More specifically, the dose at which the Birnavirus is to be administered amounts to between $10^6$ and $10^9$ infectious units per day. The present inventors have determined that the virus is effective at at least $10^6$ infectious units per day and safe up to $10^9$ infectious units per day. In one embodiment, the dose at which the Birnavirus is to be administered amounts to $\geq 10^6$ infectious units and $<10^8$ infectious units per day, especially for a maximum of 1 week. In one embodiment, the dose at which the Birnavirus is to be administered amounts to $\geq 10^6$ infectious units and $<10^7$ infectious units once (also dividable into two portions), $\geq 10^6$ infectious units and $<10^7$ infectious units twice within 48 hours, 24 hours, or $\geq 10^6$ infectious units and $<10^7$ infectious units thrice within 72 hours. In one embodiment, the dose at which the Birnavirus is to be administered amounts to $\geq 10^6$ infectious units and $<10^7$ infectious units once.

The pharmaceutical composition in accordance with the present invention may comprise one or more excipient(s), diluent(s), and/or carrier(s), all of which are pharmaceutically acceptable. The term "pharmaceutically acceptable", as used herein, means approved by a regulatory agency of the Federal or a state government or listed in the U.S. Pharmacopeia, European Pharmacopeia (Ph. Eur.) or other generally recognized pharmacopeia for use in animals, and more particularly in humans.

The term "excipient", as used herein, is intended to indicate all substances in a pharmaceutical composition which are not active ingredients such as binders, lubricants, thickeners, surface active agents, preservatives, emulsifiers, buffers, flavoring agents, or colorants.

The term "diluent", as used herein, relates to a diluting and/or thinning agent. Moreover, the term "diluent" includes a solution, suspension (e.g., liquid or solid suspension) and/or media.

The term "carrier", as used herein, relates to one or more compatible solid or liquid fillers, which are suitable for an administration, e.g., to a human. The term "carrier" relates to a natural or synthetic organic or inorganic component which is combined with an active component in order to facilitate the application of the active component. In some embodiments, carrier components are sterile liquids such as water or oils, including those which are derived from mineral oil, animals, or plants, such as peanut oil, soybean oil, sesame oil, sunflower oil, etc. Salt solutions and aqueous dextrose and glycerin solutions may also be used as aqueous carrier compounds.

Pharmaceutically acceptable carriers or diluents for therapeutic use are well known in the pharmaceutical art, and are described, for example, in Remington's Pharmaceutical Sciences, Mack Publishing Co. (A. R Gennaro edit. 1985). Examples of suitable carriers include, for example, magnesium carbonate, magnesium stearate, talc, lactose, pectin, dextrin, starch, gelatin, tragacanth, methylcellulose, sodium carboxymethylcellulose, a low melting wax, cocoa butter, and the like. Examples of suitable diluents include ethanol, glycerol, and water.

Pharmaceutical carriers, diluents, and/or excipients can be selected with regard to the intended route of administration and standard pharmaceutical practice. The pharmaceutical compositions of the present invention may comprise as, or in addition to, the carrier(s), excipient(s) or diluent(s) any suitable binder(s), lubricant(s), suspending agent(s), coating agent(s), and/or solubilizing agent(s). Examples of suitable binders include starch, gelatin, natural sugars such as glucose, lactose, sucrose, trehalose, corn sweeteners, natural and synthetic gums, such as acacia, tragacanth or sodium alginate, carboxymethyl cellulose, and polyethylene glycol. Examples of suitable lubricants include sodium oleate, sodium stearate, magnesium stearate, sodium benzoate, sodium acetate, sodium chloride, and the like. Preservatives, stabilizers, dyes, and even flavoring agents may be provided in the pharmaceutical composition. Examples of preservatives include sodium benzoate, sorbic acid, and esters of p-hydroxybenzoic acid. Antioxidants and suspending agents may be also used.

The term "systemic administration", a used herein, refers to the administration of the Birnavirus, the combination comprising at least one Birnavirus and at least one further active agent, or the pharmaceutical composition comprising the Birnavirus or the combination such that said Birnavirus, combination, or pharmaceutical composition becomes widely distributed in the body of a subject in significant amounts and develops a biological effect. Typical systemic routes of administration include administration by introducing the Birnavirus, the combination comprising at least one Birnavirus and at least one further active agent, or the pharmaceutical composition comprising the Birnavirus or the combination directly into the vascular system, wherein said Birnavirus, combination, or pharmaceutical composition enters the vascular system and is carried to one or more desired site(s) of action via the blood. The systemic administration may be by parenteral administration.

The term "parenteral administration", as used herein, refers to the administration of the Birnavirus, the combination comprising at least one Birnavirus and at least one further active agent, or the pharmaceutical composition comprising the Birnavirus or the combination such that said Birnavirus, combination, or pharmaceutical composition does not pass the intestine. The term "parenteral administration" includes intravenous administration, subcutaneous administration, intradermal administration, or intraarterial administration, but is not limited thereto. The Birnavirus, the combination comprising at least one Birnavirus and at least one further active agent, or a pharmaceutical composition comprising the Birnavirus or the combination is administered orally, nasally, or by inhalation.

The term "subject", as used herein, refers to any individual which may receive a Birnavirus, a combination comprising at least one Birnavirus and at least one further active agent, or a pharmaceutical composition comprising the Birnavirus or the combination of the present invention. The term "subject", as used herein, refers to any individual that/who may benefit from the treatment with a Birnavirus, a combination comprising at least one Birnavirus and at least one further active agent, or a pharmaceutical composition comprising the Birnavirus or the combination of the present invention. The subject suffers from a disease caused by a Varicella zoster virus. The subject is treated for a disease caused by a Varicella zoster virus.

The subject may be a vertebrate, e.g., a human being, dog, cat, sheep, goat, cow, horse, camel or pig. It some embodiments, the "subject" is a human being.

The terms "subject", "individual", or "patient" are used interchangeably herein.

In the context of the present invention, the term "kit of parts (in short: kit)" is understood to be any combination of at least some of the components identified herein, which are combined, coexisting spatially, to a functional unit, and which can contain further components.

Compositions and Methods of Treatment.

Herpes zoster (shingles) is caused by the Herpes Zoster virus and characterized by pain and unilateral vesicular rash that typically affects one dermatome. Symptoms tend to resolve over 10-15 days. The present disclosure provides a case report of the treatment of a 75-year-old subject with herpes zoster ophthalmicus with severe orbital edema. The upper eyelid and the proximal nasal area were also affected. The subject felt intermittent throbbing pain in more than three dermatomes including the frontal, orbital, temporal and occipital/nuchal areas. Since the prodromal and erythematous phase started with atypical signs, conventional acyclovir treatment was administered only 96 hours after the first symptoms. Acyclovir treatment was therefore complemented with the experimental viral superinfection therapy. Superinfection is a host directed therapy during which, the non-pathogenic avian live attenuated infectious bursal disease vaccine virus delivers its double-stranded RNA (dsRNA) cargo to host cells and activates their natural antiviral interferon gene defense system from within. Most symptoms were resolved within five days. At 75 years of age, such a complete and rapid recovery is unlikely to be explained by the belated acyclovir treatment alone.

Thus, embodiments of the present disclosure provide individual clinical insights that are missed in clinical trials. Breakthrough cases paved the way for revolutionary medical advances, such as, for example, the first cord blood (CB) transplant which was performed in 1988 in a patient with Fanconi anemia. Since then, CB transplantation became standard therapy. The first advanced leukemia patient who was cured by the experimental chimeric antigen receptor (CAR) T cell therapy became a promising treatment modality. Considering the fact that IBDV superinfection (SIT) has been demonstrated to be clinically effective in HAV, HBV, HCV and SARS-CoV-2 infections, the unexpectedly rapid recovery from a Herpes zoster ophthalmicus (HZO) infection reported herein will hopefully start a debate about the potential application of IBDV for the adjuvant treatment of severe herpes zoster, including HZO.

Early diagnosis and prompt treatment of shingles in the prodromal phase by anti-viral agents has the highest chance of efficacy. In most individual studies of herpes zoster, the time required for the vesicles, ulcers, and crusts to resolve was shorter when antiviral medication was used compared to placebo but only by 1 or 2 days. Quicker healing of skin lesions was not observed. The efficacy of acyclovir treatment (800 mg, five times daily, for seven days) initiated more than 72 hours after the onset of skin rash has, however, never been confirmed. Furthermore, healing may take longer in older patients. Antiviral medicines may still be considered up to seven days after onset of symptoms if the patient has an increased risk of severe disease due to his/her older age or threatening complications, such as the ophthalmic involvement or post-herpetic neuralgia (PHN). PHN is observed in well over 50% of patients with HZO and can be severe and long-lasting. Scarring also is more common in HZO, probably due to the severe destructive inflammation. Therefore, as described further herein, acyclovir treatment was started despite that the first symptoms occurred 96 hours earlier. Similarly, as described further herein, the subject complemented the conventional treatment with experimental viral (IBDV) superinfection therapy (SIT) despite the fact that the treatment of herpes zoster with IBDV has never previously been tested.

SIT is a host-directed therapy (HDT) during which the non-pathogenic avian attenuated infectious bursal disease virus (IBDV) delivers its double-stranded RNA (dsRNA) cargo to host cells and activates their natural antiviral interferon gene defense system from within. Activation is induced via Toll-like receptors (TLRs), which are a family of innate immune-recognition receptors that recognize molecular patterns associated with microbial pathogens. As most viruses produce dsRNA at some point during their replication cycle, dsRNA is a molecular pattern that is associated with viral infection. Attenuated IBDV vaccine strains genomes are composed of dsRNA. IBDV has previously successfully treated hepatitis A virus (HAV) infection in marmoset monkeys and in patients with acute and chronic (decompensated) hepatitis B virus (HBV) and hepatitis C virus (HCV) infection. Importantly, the patients with decompensated liver disease had high-level viremia, which is one of the key drivers of cytokine storm. IBDV treatment however did not induce excessive release of pro-inflammatory cytokines.

The safety of SIT is in sharp contrast to the toxicity of systemic IFN-based therapy that causes significant morbidity requiring dose reduction or even discontinuation of treatment. One possible explanation for this difference could be the contrasting target ranges of the two therapies. Systemic IFN therapy has the almost ubiquitous characteristic of broad immune signaling because receptors for type I and type II IFNs are found on the surface of most human cells. In contrast, following host cell exposure to IBDV, its dsRNA is recognized by specific receptors (e.g., TLR3), which activate several gene families from within.

Figure 7:
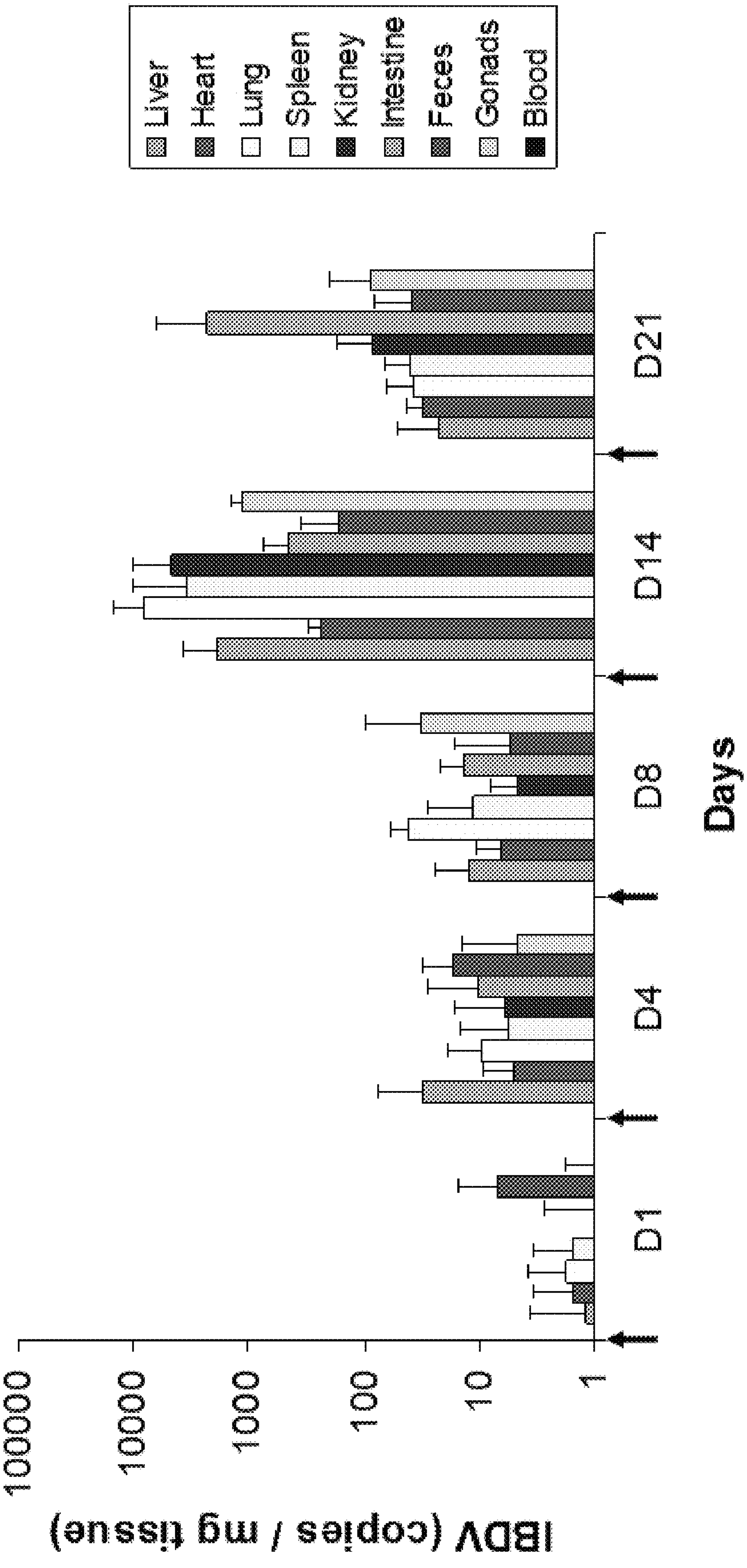
FIG. 7: Balb/C mice were dosed with multiple oral delivery of $1.7\times10^6$ IU of IBDV at days 0, 3, 7, 13, and 20 (indicated with arrows). Necropsy was performed on days 1, 4, 8, 14, and 21. Tissue RNA was quantified by quantitative real-time RT-PCR. The transduction efficiency is expressed as IBDV copy numbers per mg of tissue. Each bar represents the arithmetic mean of four independent experiments, except D21, where 1 mouse died. Error bars indicate the standard error deviation (±SD; n=4; n=3 for D21). Reproduced with slight modification from Hornyak, et al., J Gene Med 2015, 17, 116 with permission from John Wiley & Sons, Ltd. (License Number: 5176880126861).

In this context, it is important to recall that we investigated the biodistribution of IBDV following multiple oral administrations in mice, which was assessed in multiple organs using qRT-PCR. Despite the presence of high levels of neutralizing antibodies there was a substantial increase in virus copy numbers in most organs. The highest amounts of virus RNA were detected in the liver, spleen, lung and kidney (FIG. 7).

These data indicated viral stability and genome accumulation under the multiple dosing scenario rather than viral replication in mouse tissues. This is consistent with clinical observations in decompensated hepatitis patients, when large doses of the viral preparation were administered continuously over a long period to ensure maintenance of "artificial viremia" by IBDV, which is not known to infect human beings naturally. The presence of the virus in the nervous system was not evaluated. The current clinical observation would however encourage the extension of the biodistribution study to the cell bodies of neurons and the skin.

IBDV is simple to manufacture and will be affordable even in resource limited countries. Acid resistant IBDV can be orally administered in an outpatient setting providing the greatest ease of dosing and the highest chance of patient compliance. The German Paul Ehrlich Institute supports a phase I safety study for persons acutely infected with SARS-CoV-2. An expert team of the US National Institutes of Health-sponsored ACTIV public-private partnership came to the conclusion that the IBDV drug candidate shows merit as a potential treatment for COVID-19 (personal communication from Joseph P. Menetski, PhD Associate Vice President Research Partnerships Foundation for the National Institutes of Health, Inc.). An FDA approved clinical COVID-19 trial is in preparation in Los Angeles.

As described further herein, the rapid recovery of the subject was unexpected given that the entire disease course was usually 5-6 weeks, in which the ulcerous phase was the longest, more than 2 weeks. Acyclovir given even at the onset of the earliest symptoms could only modify the symptoms but would not be able to change the duration of the disease course. In this context, the duration of the subject's case seems to be very unusual. The onset of vesicles was typical but the severe orbital edema was an early sign of the severity of the HZO. In contrast, the fast resolution of the orbital edema and the very quick crusting of vesicles cannot be explained by the acyclovir treatment alone. Consistent with this, in two cases of elderly patients with facial herpes zoster (without HZO) who were treated with valacyclovir and acyclovir, respectively, complete regression was seen after 2 weeks.

In accordance with the above, embodiments of the present disclosure include a composition comprising a strain of an Infectious Bursal Disease Virus (IBDV) for the treatment of disease caused by a Varicella zoster virus (VZV). In some embodiments, the IBDV is derived from a recombinant Birnavirus, or any derivative or variant thereof. In some embodiments, the IBDV is an IBDV of strain 903/78 (also referred to as V903/78 or R903/78). In accordance with these embodiments, the disease caused by the VZV can be herpes zoster. In some embodiments, the disease caused by the VZV is herpes zoster ophthalmicus.

In some embodiments, the IBDV is derived from non-pathogenic attenuated strain 903/78 and comprises a nucleic acid sequence that is at least 80% identical to SEQ ID NO: 1 (segment A). In some embodiments, the IBDV is derived from non-pathogenic attenuated strain 903/78 and comprises a nucleic acid sequence that is at least 85% identical to SEQ ID NO: 1 (segment A). In some embodiments, the IBDV is derived from non-pathogenic attenuated strain 903/78 and comprises a nucleic acid sequence that is at least 90% identical to SEQ ID NO: 1 (segment A). In some embodiments, the IBDV is derived from non-pathogenic attenuated strain 903/78 and comprises a nucleic acid sequence that is at least 91% identical to SEQ ID NO: 1 (segment A). In some embodiments, the IBDV is derived from non-pathogenic attenuated strain 903/78 and comprises a nucleic acid sequence that is at least 92% identical to SEQ ID NO: 1 (segment A). In some embodiments, the IBDV is derived from non-pathogenic attenuated strain 903/78 and comprises a nucleic acid sequence that is at least 93% identical to SEQ ID NO: 1 (segment A). In some embodiments, the IBDV is derived from non-pathogenic attenuated strain 903/78 and comprises a nucleic acid sequence that is at least 94% identical to SEQ ID NO: 1 (segment A). In some embodiments, the IBDV is derived from non-pathogenic attenuated strain 903/78 and comprises a nucleic acid sequence that is at least 95% identical to SEQ ID NO: 1 (segment A). In some embodiments, the IBDV is derived from non-pathogenic attenuated strain 903/78 and comprises a nucleic acid sequence that is at least 96% identical to SEQ ID NO: 1 (segment A). In some embodiments, the IBDV is derived from non-pathogenic attenuated strain 903/78 and comprises a nucleic acid sequence that is at least 97% identical to SEQ ID NO: 1 (segment A). In some embodiments, the IBDV is derived from non-pathogenic attenuated strain 903/78 and comprises a nucleic acid sequence that is at least 98% identical to SEQ ID NO: 1 (segment A). In some embodiments, the IBDV is derived from non-pathogenic attenuated strain 903/78 and comprises a nucleic acid sequence that is at least 99% identical to SEQ ID NO: 1 (segment A). In some embodiments, the IBDV is derived from non-pathogenic attenuated strain 903/78 and comprises a nucleic acid sequence that is 100% identical to SEQ ID NO: 1 (segment A).

In some embodiments, the IBDV is derived from non-pathogenic attenuated strain 903/78 and comprises a nucleic acid sequence that is at least 80% identical to SEQ ID NO: 2 (segment B). In some embodiments, the IBDV is derived from non-pathogenic attenuated strain 903/78 and comprises a nucleic acid sequence that is at least 85% identical to SEQ ID NO: 2 (segment B). In some embodiments, the IBDV is derived from non-pathogenic attenuated strain 903/78 and comprises a nucleic acid sequence that is at least 90% identical to SEQ ID NO: 2 (segment B). In some embodiments, the IBDV is derived from non-pathogenic attenuated strain 903/78 and comprises a nucleic acid sequence that is at least 91% identical to SEQ ID NO: 2 (segment B). In some embodiments, the IBDV is derived from non-pathogenic attenuated strain 903/78 and comprises a nucleic acid sequence that is at least 92% identical to SEQ ID NO: 2 (segment B). In some embodiments, the IBDV is derived from non-pathogenic attenuated strain 903/78 and comprises a nucleic acid sequence that is at least 93% identical to SEQ ID NO: 2 (segment B). In some embodiments, the IBDV is derived from non-pathogenic attenuated strain 903/78 and comprises a nucleic acid sequence that is at least 94% identical to SEQ ID NO: 2 (segment B). In some embodiments, the IBDV is derived from non-pathogenic attenuated strain 903/78 and comprises a nucleic acid sequence that is at least 95% identical to SEQ ID NO: 2 (segment B). In some embodiments, the IBDV is derived from non-pathogenic attenuated strain 903/78 and comprises a nucleic acid sequence that is at least 96% identical to SEQ ID NO: 2 (segment B). In some embodiments, the IBDV is derived from non-pathogenic attenuated strain 903/78 and comprises a nucleic acid sequence that is at least 97% identical to SEQ ID NO: 2 (segment B). In some embodiments, the IBDV is derived from non-pathogenic attenuated strain 903/78 and comprises a nucleic acid sequence that is at least 98% identical to SEQ ID NO: 2 (segment B). In some embodiments, the IBDV is derived from non-pathogenic attenuated strain 903/78 and comprises a nucleic acid sequence that is at least 99% identical to SEQ ID NO: 2 (segment B). In some embodiments, the IBDV is derived from non-pathogenic attenuated strain 903/78 and comprises a nucleic acid sequence that is 100% identical to SEQ ID NO: 2 (segment B).

In some embodiments, the IBDV is administered to a subject in need thereof as a pharmaceutically acceptable formulations. In some embodiment, the IBDV is formulated for administration to a subject receiving or having received treatment for VZV. In some embodiments, the VZV treatment is selected from the group consisting of an antiviral drug therapy, an antibacterial drug therapy, an anti-inflammatory drug therapy, antifungal drug therapy, an antipyretic agent therapy, and corticoid therapy. In some embodiments, the VZV treatment comprises administration of acyclovir.

As described further herein, embodiments of the present disclosure also include a method of treating a subject having or suspected of having a disease caused by a Varicella zoster virus (VZV). In accordance with these embodiments, the method includes administering a therapeutically effective dose of composition comprising a strain of an Infectious Bursal Disease Virus (IBDV), and at least one pharmaceutically acceptable carrier or excipient. In some embodiments of the method, the disease caused by the VZV is herpes zoster. In some embodiments of the method, the disease caused by the VZV is herpes zoster ophthalmicus.

In some embodiments of the method, the composition is administered intravenously, subcutaneously, intradermally, intraarterially, orally, nasally, and/or by inhalation. In some embodiments of the method, the composition is administered orally. In some embodiments of the method, the composition is administered at a dose ranging from about $10^6$ to about $10^9$ infectious units per day. In some embodiments of the method, as described above, the IBDV is derived from non-pathogenic attenuated strain 903/78 and comprises a nucleic acid sequence that is at least 80%, and up to 100%, identical to SEQ ID NO: 1 (segment A). In some embodiments of the method, as described above, the IBDV is derived from non-pathogenic attenuated strain 903/78 and comprises a nucleic acid sequence that is at least 80%, and up to 100%, identical to SEQ ID NO: 2 (segment B).

In some embodiments of the method, the method further comprises administering a VZV treatment selected from the group consisting of an antiviral drug therapy, an antibacterial drug therapy, an anti-inflammatory drug therapy, antifungal drug therapy, an antipyretic agent therapy, and corticoid therapy. In some embodiments of the method, the method further comprises administration of acyclovir. In some embodiments of the method, the method treats at least one symptom associated with the VZV disease in the subject.

In accordance with the above, it was surprisingly found that viruses of the Birnaviridae family can be used as a medicament; specifically, as medicament for therapy of diseases caused by a VZV. In particular, it was found that viruses of the Birnaviridae family promote activation of the interferon-dependent antiviral gene program and, thus, allow an efficient treatment of a broad range of different VZV infections/diseases. Thus, in a first aspect, the present invention relates to a Birnavirus for use in the treatment of a disease caused by a VZV. In one embodiment, the Birnavirus is selected from the group consisting of an avibirnavirus, an aquabirnavirus, a blosnavirus, a dronavirus, an entomobirnavirus, a ronavirus, and a telnavirus.

In one embodiment, the avibirnavirus is an Infectious Bursal Disease Virus (IBDV). In one embodiment, the IBDV is an IBDV of strain 903/78. In one embodiment, the IBDV of strain 903/78 comprises a nucleotide sequence according to SEQ ID NO: 1, a fragment thereof or a sequence having at least 80% sequence identity thereto, and/or a nucleotide sequence according to SEQ ID NO: 2, a fragment thereof or a sequence having at least 80% sequence identity thereto. In some embodiments, the Birnavirus is a live and/or attenuated Birnavirus. The Birnavirus may be a naturally occurring or non-naturally occurring (live and/or attenuated) Birnavirus. The non-naturally occurring Birnavirus is a recombinant Birnavirus. The naturally or non-naturally occurring Birnavirus may be rescued from a bacterial plasmid designed for expression of Birnavirus RNAs. The non-naturally occurring (recombinant) Birnavirus is a mutated Birnavirus or a chemically treated Birnavirus (e.g., treated with a protease).

By using the clinically proven attenuated live avian virus IBDV R903/78 for the treatment of a disease caused by a VZV (e.g., shingles), it was surprisingly found that a dose of at least $10^6$ infectious units per day is effective in the treatment of a disease caused by a VZV in humans and that a dose of $10^9$ infectious units per day is still safe for humans. Thus, the dose at which the Birnavirus is to be administered specifically amounts to at least $10^6$ infectious units per day. More specifically, the dose at which the Birnavirus is to be administered amounts to between $10^6$ and $10^9$ infectious units per day. It should be noted that the above doses are to be administered for no more than/for a maximum of 1 week, e.g., for 1, 2, 3, 4, 5, 6, or 7 day(s).

In one embodiment, the dose at which the Birnavirus is to be administered amounts to $\geq 10^6$ infectious units and $<10^7$ infectious units per day. In one embodiment, the dose at which the Birnavirus is to be administered amounts to $\geq 10^6$ infectious units and $<10^7$ infectious units per day for no more than/for a maximum of 1 week, e.g., for 1, 2, 3, 4, 5, 6, or 7 day(s). In one even embodiment, the dose at which the Birnavirus is to be administered amounts to $\geq 10^6$ infectious units and $<10^7$ infectious units once (also dividable into two portions), $\geq 10^6$ infectious units and $<10^7$ infectious units twice within 48 hours, 24 hours, or $\geq 10^6$ infectious units and $<10^7$ infectious units thrice within 72 hours. In one still even embodiment, the dose at which the Birnavirus is to be administered amounts to $\geq 10^6$ infectious units and $<10^7$ infectious units once. In some embodiments, the above-described doses are to be administered within 1 week after the first sign(s)/symptom(s) of a disease caused by a VZV (e.g., shingles). For example, the above-described doses are to be administered after 1, 2, 3, 4, 5, 6, or 7 day(s) after the first sign(s)/symptom(s) of a disease caused by a VZV. In some embodiments, the above-described doses are to be administered immediately after the first sign(s)/symptom(s) of a disease caused by a VZV.

Thus, in one embodiment, the dose at which the Birnavirus is to be administered amounts to $\geq 10^6$ infectious units and $<10^7$ infectious units per day, wherein the dose is to be administered within 1 week after the first sign(s)/symptom(s) of a disease caused by a VZV, e.g., after 1, 2, 3, 4, 5, 6, or 7 day(s). In one embodiment, the dose at which the Birnavirus is to be administered amounts to $\geq 10^6$ infectious units and $<10^7$ infectious units per day for no more than/for a maximum of 1 week, wherein the dose is to be administered within 1 week after the first sign(s)/symptom(s) of a disease caused by a VZV, e.g. after 1, 2, 3, 4, 5, 6, or 7 day(s). In one embodiment, the dose at which the Birnavirus is to be administered amounts to $\geq 10^6$ infectious units and $<10^7$ infectious units once (also dividable into two portions), $\geq 10^6$ infectious units and $<10^7$ infectious units twice within 48 hours, 24 hours, or $\geq 10^6$ infectious units and $<10^7$ infectious units thrice within 72 hours, wherein the dose is to be administered within 1 week after the first sign(s)/symptom(s) of a disease caused by a VZV, e.g. after 1, 2, 3, 4, 5, 6, or 7 day(s). In one embodiment, the dose at which the Birnavirus is to be administered amounts to $\geq 10^6$ infectious units and $<10^7$ infectious units once, wherein the dose is to be administered within 1 week after the first sign(s)/symptom(s) of a disease caused by a VZV, e.g., after 1, 2, 3, 4, 5, 6, or 7 day(s).

In addition to the first appearance of VZV disease symptoms as a signal to start therapy, a positive VZV disease test result can also mark the start of therapy. In one embodiment, the Birnavirus is for administration to a subject receiving or having received at least one further therapy against a disease caused by a VZV (e.g., shingles). In this regard, the administration of the Birnavirus is considered to be a first therapy against a disease caused by a VZV and the further therapy against a disease caused by a VZV is considered to be a second therapy against a disease caused by a VZV. In one embodiment, the at least one further therapy against a disease caused by a VZV is selected from the group consisting of an antiviral drug therapy, an antibacterial drug therapy, an anti-inflammatory drug therapy, antifungal drug therapy, an antipyretic agent therapy, and a corticoid therapy. However, also (additionally or alternatively) another treatment than a drug therapy is possible.

In some embodiments, the Birnavirus is administered in a therapeutically effective amount. It is (alternatively or additionally) further contemplated that the subject is treated with the Birnavirus prior to, during and/or after the subject was subjected to at least one further therapy against a disease caused by a VZV. In some embodiments, the at least one further therapy against a disease caused by a VZV is selected from the group consisting of an antiviral drug therapy, an antibacterial drug therapy, an anti-inflammatory drug therapy, antifungal drug therapy, an antipyretic agent therapy, and a corticoid therapy.

In come embodiments, the Birnavirus is administered to a subject as a pharmaceutical composition comprising one or more pharmaceutical acceptable excipient(s), diluent(s), and/or carrier(s). The pharmaceutical composition can be administered systemically, e.g., parenterally. In one embodiment, the pharmaceutical composition is in a form suitable for oral administration, nasal administration, or administration by inhalation. The pharmaceutical composition can also be administered intravascular, intravenous, intramuscular, intrathecal, subcutaneous, or intraperitoneal. The pharmaceutical composition can be administered in a single dose or in more than one dose. In some embodiments, the pharmaceutical composition is to be administered in a therapeutically effective amount.

The following examples further illustrate the invention but, of course, should not be construed as in any way limiting its scope.

EXAMPLES

In accordance with the above embodiments, described herein is a case report of a subject that experienced an unexpectedly rapid recovery from a Herpes zoster ophthalmicus (HZO) infection upon treatment with a non-pathogenic avian attenuated infectious bursal disease virus (IBDV). More specifically, the subject had varicella at age 9. Then, at age 75, experienced a first herpes zoster episode. The subject reported no chronic disease and reported doing regular physical exercise 6 days a week, and is otherwise in good physical condition. VZV was probably reactivated by an hour-long tooth extraction three days before the first herpes symptoms occurred (Sep. 30, 2021; see FIG. 1).

The prodromal, erythematous and macular phase was quite atypical at the beginning. The subject felt only a localized tingling, itching but not yet burning sensation at the left side on the top of his head (October 2). Within a few days, however, the rash became painful and spread to the left face including the periorbital area (Oct. 5, 2021). Importantly, the upper eyelid below the palpebral fissure and the proximal nasal area were also involved. By this time, many erythematous papules appeared that developed into vesicles which begun to pustulate and became ulcerated (FIG. 2).

The subject felt intermittent throbbing pain on the frontal, periorbital, temporal and occipital/nuchal areas. The pain was tolerable but it persisted through all the symptomatic stages of the shingles episode. The subject also had systemic symptoms, including malaise, fever and headache. An ipsilateral preauricular lymph node became also palpable.

Due to the atypical mild syndromes during the first few days, the subject did not recognize that he had shingles and therefore started conventional standard acyclovir treatment belatedly, 96 hours after the first symptoms (Oct. 7, 2021) (EGIS Inc, 5×800 mg daily, for seven days). However, when the rash and vesicles expanded to the periorbital region including the upper palpebra with a fast-increasing edema around the eye (see FIG. 2) accompanied with strong yellow discharge, the subject realized that he had HZO. Importantly, the neuralgia affected the ophthalmic (V1), maxillary (V2), lesser occipital (ventral ramus C2), and greater occipital (dorsal rami C2 & C3) dermatomes, respectively. As the posterior scalp (nuchal area) was involved in the neuralgia, herpes occipiticollaris may also be suspected. Herpes involving all three branches of the trigeminal nerve is known as disseminated zoster and seen in immunocompromised patients but in immunocompetent individuals this is a rarity.

The subject is experienced with the development of broad-spectrum viral superinfection therapy (SIT) for the post-infection treatment of viral diseases. SIT is a host-directed therapy during which the non-pathogenic avian live attenuated infectious bursal disease vaccine virus delivers its double-stranded RNA (dsRNA) cargo to host cells and activates their natural antiviral interferon gene defense system from within. Therefore, the subject complemented the acyclovir treatment with SIT (Oct. 8, 2021). Although, the subject had no experience with herpes zoster infections, based on prior investigations demonstrating that oral treatment with IBDV is safe and potentially effective for treatment of other viral infections, the subject self-administered an oral dose of avian attenuated live IBDV vaccine virus at $2\times10^6$ IU/day ($10^6$ IU=$10^6$ $TCID_{50}$ [TCID=tissue culture infective dose]) for 3 days, and then $10^6$ IU/day for one more day ($7\times10^6$ IU in total). (On October 18$^{th}$ the subject restarted IBDV treatment ($10^6$ IU/day) for 7 days ($7\times10^6$ IU in total) in order to mitigate the post-herpetic neuralgia (PHN).) The orbital edema rapidly decreased by IBDV treatment and crusting of the ulcerated vesicle started (FIGS. 3-5). Eventually, the rash has almost completely subsided by Oct. 12, 2021 (see FIG. 6). A slit-lamp examination by an ophthalmologist excluded corneal tissue ulcerations. Since PHN is observed in well over 50% of patients with HZO and can be severe and long-lasting, IBDV treatment likely shortened the duration of PHN. The only adverse event of SIT was a slight rise of temperature (up to 37.5° C.) following the oral administration of IBDV, which is well-known in other patients.

What is claimed is:

1. A method of treating a subject having or suspected of having a disease caused by a Varicella zoster virus (VZV), the method comprising:

administering to the subject a therapeutically effective dose of a composition comprising an Infectious Bursal Disease Virus (IBDV), wherein the IBDV is non-pathogenic attenuated strain 903/78, and at least one pharmaceutically acceptable carrier or excipient.

2. The method of claim 1, wherein the disease caused by the VZV is herpes zoster.

3. The method of claim 1, wherein the disease caused by the VZV is herpes zoster ophthalmicus.

4. The method of claim 1, wherein the composition is administered intravenously, subcutaneously, intradermally, intraarterially, orally, nasally, and/or by inhalation.

5. The method of claim 1, wherein the composition is administered at a dose ranging from about $10^6$ to about $10^9$ infectious units per day.

6. The method of claim 1, wherein the method further comprises administering a VZV treatment selected from the group consisting of an antiviral drug therapy, an antibacterial drug therapy, an anti-inflammatory drug therapy, antifungal drug therapy, an antipyretic agent therapy, and corticoid therapy.

7. The method of claim 1, wherein the method further comprises administration of acyclovir.

8. The method of claim 1, wherein the method treats at least one symptom associated with the VZV disease in the subject.

* * * * *

SEQUENCE LISTING

```
Sequence total quantity: 2
SEQ ID NO: 1          moltype = DNA  length = 3258
FEATURE               Location/Qualifiers
source                1..3258
                      mol_type = other DNA
                      organism = Infectious bursal disease virus
SEQUENCE: 1
ggatacgatc ggtctgaccc cgggggagtc acccggggac aggccgtcaa ggctttgttc  60
caggatggaa ctcctccttc tacaacgcta tcattgatgg tcagtagaga tcagacaaac  120
gatcgcagcg atgacaaacc tgcaagatca aacccaacag attgttccgt tcatacggag  180
ccttctgatg ccaacaaccg gaccggcgtc cattccggac gacaccctgg agaagcacac  240
tctcaggtca gagacctcga cctacaattt gactgtgggg gacacagggt cagggctaat  300
tgtctttttc cctggattcc ctggctcaat tgtgggtgct cactacacac tgcagagcaa  360
tgggaactac aagttcgatc agatgctcct gactgcccag aacctaccgg ccagttacaa  420
ctactgcagg ctagtgagtc ggagtctcac agtgaggtca agcacacttc ctggtggcgt  480
ttatgcacta aacggcacca taaacgccgt gaccttccaa ggaagcctga gtgaactgac  540
agatgttagc tacaatgggt tgatgtctgc aacagccaac atcaacgaca aaattgggaa  600
cgtcctagta ggggaagggg tcaccgtcct cagcttaccc acatcatatg atcttgggta  660
tgtgaggctt ggtgacccca ttcccgcaat agggcttgac ccaaaaatgg tagccacatg  720
tgacagcagt gacaggccca gagtctacac cataactgca gccgatgatt accaattctc  780
atcacagtac caaccaggtg gggtaacaat cacactgttc tcagccaaca ttgatgccat  840
cacaagcctc agcgttgggg gagagctcgt gtttcaaaca agcgtccacg gcattgtact  900
gggcgccacc atctacctca taggctttga tgggacagcg gtaatcacca gggctgtggc  960
cgcaaacaat gggctgacga ccggcaccga caaccttatg ccattcaatc ttgtgattcc  1020
aacaaacgag ataacccagc caatcacatc catcaaactg gagatagtga cctccaaaag  1080
tggtggtcag gcaggggatc agatgtcatg gtcggcaaga gggagcctag cagtgacgat  1140
ccatggtggc aactatccag gggccctccg tcccgtcacg ctagtggcct acgaaagagt  1200
ggcaacagga tccgtcgtta cggtcgctgg ggtgagcaac ttcgagctga tcccaaatcc  1260
tgaactagca aagaacctgg ttacagaata cggccgattt gacccaggag ccatgaacta  1320
cacaaaattg atactgagtg agagggaccg tcttggcatc aagaccgtct ggccaacaag  1380
ggagtacact gactttcgtg aatacttcat ggaggtggcc gacctcaact ctcccctgaa  1440
gattgcagga gccttcggct tcaaagacat aatccgggcc ataaggagga tagctgtgcc  1500
ggtggtctcc acattgttcc cacctgccgc tcccctagcc catgcaattg gggaaggtgt  1560
agactacctg ctgggcgatg aggcacaggc tgcttcagga actgctcgag ccgcgtcagg  1620
aaaagcaaga gctgcctcag gccgcataag gcagctgact ctcgccgccg acaaggggta  1680
cgaggtagtc gcgaatctat tccaggtgcc ccagaatccc gtagtcgacg ggattcttgc  1740
ttcacctggg gtactccgcg gtgcacacaa cctcgactgc gtgttaagag agggtgccac  1800
gctattccct gtggttatta cgacagtgga agacgccatg acacccaaag cattgaacag  1860
caaaatgttt gctgtcattg aaggcgtgcg agaagacctc caacctccat ctcaaagagg  1920
atccttcata cgaactctct ctggacacag agtctatgga tatgctccag atggggtact  1980
tccactggag actgggagag actacaccgt tgtcccaata gatgatgtct gggacgacag  2040
cattatgctg tccaaagatc ccatacctcc tattgtggga aacagtggaa atctagccat  2100
agcttacatg gatgtgtttc gacccaaagt cccaatccat gtggctatga cgggagccct  2160
caatgcttgt ggcgagattg agaaagtaag ctttagaagc accaagctcg ccactgcaca  2220
ccgacttggc cttaagttgg ctggtcccgg agcattcgat gtaaacaccg ggcccaactg  2280
ggcaacgttc atcaaacgtt tccctcacaa tccacgcgac tgggacaggc tcccctacct  2340
caacctacca taccttccac ccaatgcagg acgccagtac caccttgcca tggctgcatc  2400
agagttcaaa gagacccccg aactcgagag tgccgtcaga gcaatggaag cagcagccaa  2460
cgtggaccca ctattccaat ctgcactcag tgtgttcatg tggctggaag agaatgggat  2520
```

-continued

```
tgtgactgac atggccaact tcgcactcag cgacccgaac gcccatcgga tgcgaaattt  2580
tcttgcaaac gcaccacaag caggcagcaa gtcgcaaagg gccaagtacg ggacagcagg  2640
ctacggagtg gaggctcggg gccccacacc agaggaagca cagagggaaa aagacacacg  2700
gatctcaaag aagatggaga ccatgggcat ctactttgca acaccagaat gggtagcact  2760
caatgggcac cgagggccaa gccccggcca gctaaagtac tggcagaaca cacgagaaat  2820
accggaccca aacgaggact atctagacta cgtgcatgca gagaagagcc ggttggcatc  2880
agaagaacaa atcctaaggg cagctacgtc gatctacggg gctccaggac aggcagagcc  2940
accccaagct ttcatagacg aagttgccaa agtctatgaa atcaaccatg gacgtggccc  3000
aaaccaagaa cagatgaaag atctgctctt gactgcgatg gagatgaagc atcgcaatcc  3060
caggcgggct ctaccaaagc ccaagccaaa acccaatgct ccaacacaga gacccccctgg  3120
tcggctgggc cgctggatca ggaccgtctc tgatgaggac cttgagtgag gctcctggga  3180
gtctcccgac accacccgcg caggtgtgga caccaattcg gccttacaac ccaaattgga  3240
tccgttcgcg ggtcccct                                                  3258

SEQ ID NO: 2           moltype = DNA  length = 2827
FEATURE                Location/Qualifiers
source                 1..2827
                       mol_type = other DNA
                       organism = Infectious bursal disease virus
SEQUENCE: 2
ggatacgatg ggtttgaccc tcagggagtc acgaattaac atggctacta ggggcgatac  60
ccgccgctgg ctgccacgtt agtggctcct cttcttgatg attctgccac catgagtgac  120
attttcaaca gtccacaggc gcgaagcacg atctcagcag cgttcggcat aaagcctact  180
gctggacaag acgtggaaga actcttgatc cctaaagttt gggtgccacc tgaggatccg  240
cttgccagcc ctagtcgact ggcaaagttc ctcagagaga acggctacaa agttttgcag  300
ccacggtctc tgcccgagaa tgaggagtat gagaccgacc aaatactccc agacttagca  360
tggatgcgac agatagaagg ggctgtttta aaacccactc tatctctccc tattggagat  420
caggagtact tcccaaagta ctacccaaca catcgcccta gcaaggagaa gcccaatgcg  480
tacccgccag acatcgcact actcaagcag atgatttacc tgtttctcca ggttccagag  540
gccaacgagg gcctaaagga tgaagtaacc ctcttgaccc aaaacataag ggacaaggcc  600
tatggaagtg ggacctacat gggacaagca actcgacttg tggccatgaa ggaggtcgcc  660
actggaagaa acccaaacaa ggatcctcta aagcttgggt acacttttga gagcatcgcg  720
cagctacttg acatcacact accggtaggc ccacccggtg aggatgacaa gccctgggtg  780
ccactcacaa gagtgccgtc acggatgttg gtgctgacgg gagacgtaga tggcgacttt  840
gaggttgaag attaccttcc caaaatcaac ctcaagtcat caagtggact accatatgta  900
ggtcgcacca aaggagagac aattggcgag atgatagcta tctcaaacca gtttctcaga  960
gagctatcaa cactgttgaa gcaaggtgca gggacaaagg ggtcaaacaa gaagaagcta  1020
ctcagcatgt taagtgacta ttggtactta tcatgcgggc ttttgtttcc aaaggctgaa  1080
aggtacgaca aaagcacatg gctcaccaag acccggaaca tatggtcagc tccatcccca  1140
acacacctca tgatctctat gatcacctgg cccgtgatgt ccaacagccc aaataacgtg  1200
ttgaacattg aagggtgtcc atcactctac aaattcaacc cgttcagagg agggttgaac  1260
aggatcgtcg agtggatatt ggccccggaa gaacccaagg ctcttgtata tgcggacaac  1320
atatacattg tccactcaaa cacgtggtac tcaattgacc tagagaaggg tgaggcaaac  1380
tgcactcgcc aacacatgca agccgcaatg tactacatac tcaccagagg gtggtcagac  1440
aacggcgacc caatgttcaa tcaaacatgg gccacctttg ccatgaacat tgcccctgct  1500
ctagtggtgg actcatcgtg cctgataatg aacctgcaaa ttaagaccta tggtcaaggc  1560
agcgggaatg cagccacgtt catcaacaac cacctcttga gcacgctagt gcttgaccag  1620
tggaacctga tgagacagcc cagaccagac agcgaggagt tcaaatcaat tgaggacaag  1680
ctaggtatca actttaagat tgagaggtcc attgatgata tcaggggcaa gctgagacag  1740
cttgtcctcc ttgcacaacc agggtacctg agtggggggg ttgaaccaga acaatccagc  1800
ccaactgttg agcttgacct actagggtgg tcagctacat acagcaaaga tctcgggatc  1860
tatgtgccgg tgcttgacaa ggaacgccta ttttgttctg ctgcgtatcc caagggagta  1920
gagaacaaga gtctcaaatc caaagtcggg atcgagcagg catacaaggt agtcaggtat  1980
gaggcgttga ggttggtagg tggttggaac tacccactcc tgaacaaagc ctgcaagaat  2040
aacgcaggcg ccgctcggcg gcatctggag gccaaggggt tcccactcga cgagttccta  2100
gccgagtggt ctgagctgtc agagttcggt gaggccttcg aaggcttcaa tatcaagctg  2160
accgtaacat ctgagagcct agccgaactg aacaagccag taccccccaa gcccccaaat  2220
gtcaacagac cagtcaacac tgggggactc aaggcagtca gcaacgccct caagaccggt  2280
cggtacagga acgaagccgg actgagtggt ctcgtccttc tagccacagc aagaagccgt  2340
ctgcaagatg cagttaaggc caaggcagaa gccgagaaac tccacaagtc caagccagac  2400
gaccccgatg cagactggtt cgaaagatca gaaactctgt cagaccttct ggagaaagcc  2460
gacatcgcca gcaaggtcgc ccactcagca ctcgtggaaa caagcgacgc tcttgaagca  2520
gttcagtcga cttccgtgta cacccccaag tacccagaag tcaagaaccc acagaccgcc  2580
tccaaccccg ttgttgggct ccacctgccc gccaagagag ccaccggtgt ccaggccgct  2640
cttctcggag caggaacgag cagaccaatg ggatggaggg ccccaacacg gtccaagaac  2700
gccgtgaaaa tggccaaacg gcggcaacgc caaaaggaga gccgctaaca gccatgatgg  2760
gaaccactca agaagaggac actaatccca gaccccgtat ccccggcctt cgcctgcggg  2820
ggccccc                                                              2827
```